US005866402A

United States Patent [19]

[11] Patent Number: 5,866,402

Innis et al.

[45] Date of Patent: Feb. 2, 1999

[54] CHIMERIC MCP AND DAF PROTEINS WITH CELL SURFACE LOCALIZING DOMAIN

[75] Inventors: Michael A. Innis, Moraga; Isabel Zaror, Orinda; Abla A. Creasey, Piedmont, all of Calif.

[73] Assignee: Chiron Corporation, Emeryville, Calif.

[21] Appl. No.: 435,149

[22] Filed: May 5, 1995

[51] Int. Cl.$^6$ .......................... C07K 19/00; C12N 15/62

[52] U.S. Cl. ...................... 435/252.3; 435/325; 530/350; 536/23.4

[58] Field of Search .......................... 530/350; 536/23.4; 435/240.2, 252.3, 320.1, 69.1, 69.7

[56] References Cited

U.S. PATENT DOCUMENTS

| | | | |
|---|---|---|---|
| 5,294,551 | 3/1994 | Farcht et al. | 435/402 |
| 5,378,614 | 1/1995 | Petersen et al. | 435/69.8 |
| 5,679,546 | 10/1997 | Ko et al. | 435/69.2 |

FOREIGN PATENT DOCUMENTS

| | | |
|---|---|---|
| 0 512 733 | 11/1992 | European Pat. Off. . |
| 91/18097 | 11/1991 | WIPO . |
| 9207935 | 5/1992 | WIPO . |
| 95/08570 | 3/1995 | WIPO . |

OTHER PUBLICATIONS

Caras et al, *Nature,* (1987) 325:545–549.
Drake et al., *J.Biol.Chem.,* (1993) 268:15859–15867.
Liszewiski et al., *Ann. Rev. Immunol.* (1991) 9:431–455.
Lublin et al, *J. Exp. Med.,* (1988) 168:181–194.
Lublin et al., *J. Exp. Med.* (1991) 174:35–44.
Medof et al, *Proc. Nat. Acad. Sci. USA* (1987) 84:2007–2011.
Moran et al, *J. Immunol.,* (1992) 149:1736–1743.
Woods et al., *Molec. Biol. Cell* (1993) 4:605–613.
Fodor et al., *J. of Immunol.,* (1995) 155(9):4135–4138.
Iwata et al. (1994) J. Immunol. 152, 3436–3444.
Cardin et al (1989) Arteriosclerosis 9, 21–32.
Sobel et al (1989) J. Biol. Chem. 267, 8857–8862.

*Primary Examiner*—David L. Fitzgerald
*Assistant Examiner*—Karen E. Brown
*Attorney, Agent, or Firm*—Ronald C. Lundquist; Paul B. Savereide; Robert P. Blackburn

[57] ABSTRACT

Chimeric proteins containing sequences from MCP and DAF and further containing peptide sequences capable of binding glycosaminoglycans. Nucleotide sequences encoding the chimeric proteins, expression vectors containing the nucleotide sequences, as well as transformed host cells capable of producing the chimeric proteins are claimed.

15 Claims, 5 Drawing Sheets

*Fig. 1A*

```
                                                MetGluProProGlyArg
CTGCTTTCCTCCGGAGAAATAACAGCGTCTTCCGCGCCGCGCATGGAGCCTCCCGGCCGC

ArgGluCysProPheProSerTrpArgPheProGlyLeuLeuLeuAlaAlaMetValLeu
CGCGAGTGTCCCTTTCCTTCCTGGCGCTTTCCTGGGTTGCTTCTGGCGGCCATGGTGTTG

LeuLeuTyrSerPheSerAspAlaCysGluGluProProThrPheGluAlaMetGluLeu
CTGCTGTACTCCTTCTCCGATGCCTGTGAGGAGCCACCAACATTTGAAGCTATGGAGCTC

IleGlyLysProLysProTyrTyrGluIleGlyGluArgValAspTyrLysCysLysLys
ATTGGTAAACCAAAACCCTACTATGAGATTGGTGAACGAGTAGATTATAAGTGTAAAAAA

GlyTyrPheTyrIleProProLeuAlaThrHisThrIleCysAspArgAsnHisThrTrp
GGATACTTCTATATACCTCCTCTTGCCACCCATACTATTTGTGATCGGAATCATACATGG

LeuProValSerAspAspAlaCysTyrArgGluThrCysProTyrIleArgAspProLeu
CTACCTGTCTCAGATGACGCCTGTTATAGAGAAACATGTCCATATATACGGGATCCTTTA

AsnGlyGlnAlaValProAlaAsnGlyThrTyrGluPheGlyTyrGlnMetHisPheIle
AATGGCCAAGCAGTCCCTGCAAATGGGACTTACGAGTTTGGTTATCAGATGCACTTTATT

CysAsnGluGlyTyrTyrLeuIleGlyGluGluIleLeuTyrCysGluLeuLysGlySer
TGTAATGAGGGTTATTACTTAATTGGTGAAGAAATTCTATATTGTGAACTTAAAGGATCA
```

*Fig. 1B*

```
ValAlaIleTrpSerGlyLysProProIleCysGluLysValLeuCysThrProProPro
GTAGCAATTTGGAGCGGTAAGCCCCCAATATGTGAAAAGGTTTTGTGTACACCACCTCCA

LysIleLysAsnGlyLysHisThrPheSerGluValGluValPheGluTyrLeuAspAla
AAAATAAAAAATGGAAAACACACCTTTAGTGAAGTAGAAGTATTTGAGTATCTTGATGCA

ValThrTyrSerCysAspProAlaProGlyProAspProPheSerLeuIleGlyGluSer
GTAACTTATAGTTGTGATCCTGCACCTGGACCAGATCCATTTTCACTTATTGGAGAGAGC

ThrIleTyrCysGlyAspAsnSerValTrpSerArgAlaAlaProGluCysLysValVal
ACGATTTATTGTGGTGACAATTCAGTGTGGAGTCGTGCTGCTCCAGAGTGTAAAGTGGTC

LysCysArgPheProValValGluAsnGlyLysGlnIleSerGlyPheGlyLysLysPhe
AAATGTCGATTTCCAGTAGTCGAAAATGGAAAACAGATATCAGGATTTGGAAAAAAATTT

TyrTyrLysAlaThrValMetPheGluCysAspLysGlyPheTyrLeuAspGlySerAsp
TACTACAAAGCAACAGTTATGTTTGAATGCGATAAGGGTTTTTACCTCGATGGCAGCGAC

ThrIleValCysAspSerAsnSerThrTrpAspProProValProLysCysLeuLysVal
ACAATTGTCTGTGACAGTAACAGTACTTGGGATCCCCCAGTTCCAAAGTGTCTTAAAGTG

SerThrAspCysGlyLeuProProAspValProAsnAlaGlnProAlaLeuGluGlyArg
TCGACTGACTGTGGCCTTCCCCCAGATGTACCTAATGCCCAGCCAGCTTTGGAAGGCCGT
```

*Fig. 1C*

ThrSerPheProGluAspThrValIleThrTyrLysCysGluGluSerPheValLysIle
ACAAGTTTTCCCGAGGATACTGTAATAACGTACAAATGTGAAGAAAGCTTTGTGAAAATT

ProGlyGluLysAspSerValIleCysLeuLysGlySerGlnTrpSerAspIleGluGlu
CCTGGCGAGAAGGACTCAGTGATCTGCCTTAAGGGCAGTCAATGGTCAGATATTGAAGAG

PheCysAsnArgSerCysGluValProThrArgLeuAsnSerAlaSerLeuLysGlnPro
TTCTGCAATCGTAGCTGCGAGGTGCCAACAAGGCTAAATTCTGCATCCCTCAAACAGCCT

TyrIleThrGlnAsnTyrPheProValGlyThrValValGluTyrGluCysArgProGly
TATATCACTCAGAATTATTTTCCAGTCGGTACTGTTGTGGAATATGAGTGCCGTCCAGGT

TyrArgArgGluProSerLeuSerProLysLeuThrCysLeuGlnAsnLeuLysTrpSer
TACAGAAGAGAACCTTCTCTATCACCAAAACTAACTTGCCTTCAGAATTTAAAATGGTCC

ThrAlaValGluPheCysLysLysLysSerCysProAsnProGlyGluIleArgAsnGly
ACAGCAGTCGAATTTTGTAAAAAGAAATCATGCCCTAATCCGGGAGAAATACGAAATGGT

GlnIleAspValProGlyGlyIleLeuPheGlyAlaThrIleSerPheSerCysAsnThr
CAGATTGATGTACCAGGTGGCATATTATTTGGTGCAACCATCTCCTTCTCATGTAACACA

GlyTyrLysLeuPheGlySerThrSerSerPheCysLeuIleSerGlySerSerValGln
GGGTACAAATTATTTGGCTCGACTTCTAGTTTTTGTCTTATTTCAGGCAGCTCTGTCCAG

*Fig. 1D*

```
TrpSerAspProLeuProGluCysArgGluIleTyrCysProAlaProProGlnIleAsp
TGGAGTGACCCGTTGCCAGAGTGCAGAGAAATTTATTGTCCAGCACCACCACAAATTGAC

AsnGlyIleIleGlnGlyGluArgAspHisTyrGlyTyrArgGlnSerValThrTyrAla
AATGGAATAATTCAAGGGGAACGTGACCATTATGGATATAGACAGTCTGTAACGTATGCA

CysAsnLysGlyPheThrMetIleGlyGluHisSerIleTyrCysThrValAsnAsnAsp
TGTAATAAAGGATTCACCATGATTGGAGAGCACTCTATTTATTGTACTGTGAATAATGAT

GluGlyGluTrpSerGlyProProProGluCysArgGlyLysSerLeuThrSerLysVal
GAAGGAGAGTGGAGTGGCCCACCACCTGAATGCAGAGGAAAATCTCTAACTTCCAAGGTC

ProProThrValGlnLysProThrThrValAsnValProThrThrGluValSerProThr
CCACCAACAGTTCAGAAACCTACCACAGTAAATGTTCCAACTACAGAAGTCTCACCAACT

SerGlnLysThrThrThrLysThrThrThrProAsnAlaGlnAlaThrArgSerThrPro
TCTCAGAAAACCACCACAAAAACCACCACACCAAATGCTCAAGCAACACGGAGTACACCT

ValSerArgThrThrLysHisPheHisGluThrThrProAsnLysGlySerGlyThrThr
GTTTCCAGGACAACCAAGCATTTTCATGAAACAACCCCAAATAAAGGAAGTGGAACCACT

SerGlyThrThrArgOP
TCAGGTACTACCCGTTGA   (SEQ ID NO: 17)
```

CHIMERIC MCP AND DAF PROTEINS WITH CELL SURFACE LOCALIZING DOMAIN

BACKGROUND OF THE INVENTION

1. Field of the Invention

The invention relates to fusion proteins containing sequences from the complement inhibitors membrane co-factor protein (hereinafter 'MCP') and decay accelerating factor (hereinafter 'DAF') wherein the fusion proteins also contain at least one cell surface localizing domain.

2. Description of the Prior Art

Complement is an important defense mechanism for warding off infectious agents. Complement works by targeting microorganisms and other antigens to complement-receptor-bearing cells, recruiting phagocytic cells to the area where complement activation is taking place and the destruction of target membrane.

Complement is a cascade of over 30 proteins and is turned on during inflammation. Indeed, the complement components C3a, C4a and C5a trigger the release of inflammatory mediators from mast cells, induce smooth muscle contraction, increase vessel permeability and recruit neutrophils. In some cases, inflammation and the accompanying activation of complement results in damage to host tissues. Sepsis, Adult Respiratory Distress Syndrome (hereinafter 'ARDS'), reperfusion injury and burns are among the clinically significant conditions in which amplification of complement activation results in tissue damage.

Complement is regulated in part by six proteins with closely related primary sequence structure including Membrane Cofactor Protein (hereinafter 'MCP') and Decay Accelerating Factor (hereinafter 'DAF'). The genes encoding MCP and DAF, as well as four other complement regulating proteins have been localized to the long arm of human chromosome 1, band 1q32. All six of these proteins have a common structural motif with an approximately 60-amino acid consensus unit or short consensus repeat (hereinafter 'SCR') and are present in four contiguous copies in MCP and DAF. Although not completely identical in sequence, the SCRs have invariant cysteines at four positions and up to 18 highly conserved positions throughout the rest of the sequence.

MCP (also known as 'CD46') is present on the cell surface of a number of cell types including peripheral blood cells (excluding erythrocytes), cells of epithelial, endothelial and fibroblast lineages, trophoblasts and sperm. MCP has four SCR sequences and serine/threonine enriched region in which heavy O-linked glycosylation occurs. MCP also has a transmembrane and cytoplasmic domain. MCP works by binding to the C3b and C4b present on the cell surface thereby targeting the protein for degradation by factor I, a plasma protease, and thereby destroying any C3 or C4 convertase activity.

Thus, MCP is said to have "cofactor activity". Because MCP is localized on the cell surface, it protects only the cells on which it is present and is therefore said to act in an intrinsic manner. The sequence of a cDNA encoding human MCP has been reported by Lublin et al, *J. Exp. Med.*, (1988) 168:181–194.

DAF is present on the cell surface of a number of cell types including peripheral blood cells (including erythrocytes), cells of epithelial, endothelial and fibroblast lineages, trophoblasts and sperm. DAF regulates complement function via "decay accelerating activity". That is, DAF binds to C4b/C2a and to C3b/Bb and destabilizes the association of C2a or Bb (the protease component) thus destroying the C3 convertase activity. DAF has also been reported to interfere with the formation of C4b/C2a and C3b/Bb complexes. As with MCP, DAF regulates complement in an intrinsic manner, thus protecting only the cells on which DAF is located.

The sequence of cDNA encoding human DAF has been reported by Medof et al, *Proc. Nat. Acad. Sci. USA* (1987) 84:2007, and by Caras et al, *Nature*, (1987) 325:545–549. The disclosure of both articles is herein incorporated by reference. Like MCP, DAF has four SCR sequences and a serine/threonine enriched region in which heavy O-linked glycosylation occurs. DAF has a cell surface localizing domain at it carboxy terminal end at which a glycophosphatidylinositol moiety (hereinafter 'GPI') is covalently bound. The GPI links DAF to cell surfaces and even allows for reattachment of DAF to cell surfaces after solubilization of cell membranes with detergent. Caras et al report the finding of two mRNAs encoding DAF. One species encodes DAF with the cell surface localizing domain. The second species accounts for 10% of DAF mRNA and appears to encode a secreted species of DAF which is lacking the cell surface localizing domain to which the GPI-anchor is attached.

This cell surface localizing domain appears to be important for the optimal function of DAF. Patients with paroxysmal nocturnal hemoglobinuria are known to be deficient in GPI-anchored proteins and this deficiency is known to causally related to susceptibility of their blood cells to lysis by complement. Moreover, Moran et al, *J. Immunol,*. (1992) 149:1736–1743 have shown that recombinant full length DAF and recombinant DAF which is missing the cell surface localizing domain (seDAF) both protect cells against complement, but that mDAF was 50 fold more potent than seDAF. However, mDAF must be incorporated into cell surface membranes to have the higher level of activity and it appears that serum lipoproteins interfere with this incorporation. This observation led Moran et al to the conclusion that seDAF will be the preferred molecule for clinical applications.

Lublin and Coyne, *J. Exp. Med.* (1991) 174:35–44 compared the activity of DAF, MCP, and variants of DAF and MCP in which the cell-surface membrane localizing domains of DAF and MCP (the GPI-anchor of DAF and the transmembrane (TM) domain of MCP) had been exchanged. Interestingly, DAF and the DAF/MCP-TM variant showed approximately equal complement inhibiting activity. Likewise, MCP and the MCP/DAF-GPI anchor variant showed approximately equal complement inhibiting activity in vitro.

Hybrid complement regulatory proteins containing DAF and MCP in a single polypeptide have been disclosed. See eg. Iwata et al, *J. Immunol.,* (1994) 152:3436–3444. Iwata et al disclose that MCP-DAF hybrids are more effective than DAF, MCP or DAF and MCP at inhibiting C3 deposition via the alternative pathway. The MCP-DAF hybrid was also more effective than MCP alone at inhibiting C3 deposition via the classical pathway.

SUMMARY OF THE INVENTION

The present invention provides chimeric proteins in which MCP, DAF and MCP-DAF hybrids are produced with cell surface localizing domains which target the molecules to cell surfaces, thereby increasing the concentration of these molecules on cell surfaces where they can act to inhibit complement-mediated cell lysis. It will be appreciated that such molecules will be useful in prevention and treatment of disease states in which complement plays a role in causing the disease state.

BRIEF DESCRIPTION OF THE DRAWINGS

FIGS. 1 and 1A–1D show a DNA sequence containing the coding region of an MCP-DAF hybrid molecule.

DETAILED DESCRIPTION OF THE INVENTION

Figure 1:
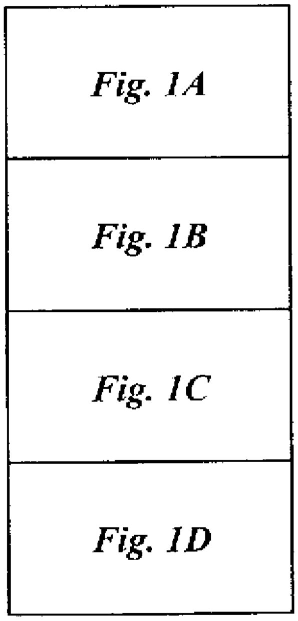

The chimeric proteins of the invention comprising MCP-DAF hybrids may be represented by the following formula:

$$A\text{-}R_1\text{-}B\text{-}R_2\text{-}C.$$

The $R_1$ component may comprise MCP or DAF. The $R_2$ component comprises DAF when $R_1$ comprises MCP and the $R_2$ component comprises MCP when $R_1$ comprises DAF. The B component may be a peptide of any length, including zero, and may or may not have biological activity including complement inhibiting activity. The flanking peptide sequences, A and C, are usually 6 or more amino acids in length and have cell surface localization properties. Alternatively, A may be a precursor sequence which is cleaved from the molecule after translation. It will be understood that A or C may be zero amino acids in length, however a peptide sequence having glycosaminoglycan binding ability will always be present in at least the A or the C position. It will be further understood that when peptide sequences are present in the A and the C positions, that A and C may be but need not be the same sequence and may have different glycosaminoglycan binding abilities.

As used herein 'MCP' means a protein having the complement inhibiting activity of mature MCP as disclosed in Lublin et al at FIG. 1 on page 184. (See below at Example 5 for assays to determine the complement-inhibiting activity of proteins containing MCP sequence). The disclosure of Lublin et al is herein incorporated by reference. It will be recognized by those skilled in the art that the entire amino acid sequence disclosed by Lublin et al will not be required for complement inhibiting activity. That is, portions of the mature MCP sequence can be deleted and yet the protein retains complement inhibiting activity. Examples of portions of MCP that could be deleted include the cytoplasmic tail and the transmembrane domain. Naturally occurring allelic variants containing amino acid substitutions retaining the complement inhibiting activity are included within the definition as are artificially produced muteins of MCP (that is, MCP with 1 to 5 amino acid substitutions). Naturally occurring and artificially produced variants of MCP, such as those described in Liszewski et al, *Ann. Rev. Immunol.,* (1991) 9:431455 and in WO 91/18097, are also included within the definition of MCP. The disclosures Liszewski et al and of WO 91/18097 are herein incorporated by reference. One portion of MCP useful in the molecules of the invention is: CysGluGluProProThrPheGluAlaMetGluLeuIleGlyLysProLysProTyr TyrGluIleGlyGluArgValAspTyrLysCysLysLysGlyTyrPheTyrIlePro ProLeuAlaThrHisThrIleCysAspArgAsnHisThrTrpLeuProValSerAsp AspAlaCysTyrArgGluThrCysProTyrIleArgAspProLeuAsnGlyGlnAla ValProAlaAsnGlyThrTyrGluPheGlyTyrGlnMetHisPheIleCysAsnGlu GlyTyrTyrLeuIleGlyGluGluIleLeuTyrCysGluLeuLysGlySerValAla IleTrpSerGlyLysProProIleCysGluLysValLeuCysThrProProProLys IleLysAsnGlyLysHisThrPheSerGluValGluValPheGluTyrLeuAspAla ValThrTyrSerCysAspProAlaProGlyProAspProPheSerLeuIleGly Glu SerThrIleTyrCysGlyAspAsnSer ValTrpSerArgAlaAlaProGluCysLys ValValLysCysArgPheProValValGluAsnGlyLysGlnIleSerGlyPheGly LysLysPheTyrTyrLysAlaThrValMetPheGluCysAspLysGlyPheTyrLeu AspGlySerAspThrIleValCysAspSerAsnSerThrTrpAspProProValPro LysCysLeuLysValSerThr (SEQ ID NO: 1)

DAF as used herein means a protein having the complement inhibiting activity of mature DAF as disclosed in Caras et al at FIG. 1*a* on page 546. The disclosure of Caras et al is herein incorporated by reference. It will be recognized by those skilled in the art that the entire amino acid sequence disclosed by Caras et al will not be required for complement inhibiting activity. That is, portions of the mature DAF sequence can be deleted and yet the protein retains complement inhibiting activity. Examples of portions of DAF that could be deleted include the GPI-anchor domain. Naturally occurring allelic variants containing amino acid substitutions retaining the complement inhibiting activity are included within the definition as are artificially produced muteins of DAF (that is, DAF with 1 to 5 amino acid substitutions). Examples of muteins may be found in EP 0 244 267. Naturally occurring variants, such as the secreted variant described by Caras et al, are included within the definition of DAF. One portion of DAF useful in the molecules of the invention is: AspCysGlyLeuProProAspValProAsnAlaGlnProAlaLeuGluGlyArgThr SerPheProGluAspThrValIleThrTyrLysCysGluGluSerPheValLysIle ProGlyGluLysAspSerValIleCysLeuLysGlySerGlnTrpSerAspIleGlu GluPheCysAsnArgSerCysGluValProThrArgLeuAsnSerAlaSerLeuLys GlnProTyrIleThrGlnAsnTyrPheProValGlyThrValValGluTyrGluCys ArgProGlyTyrArgArgGluProSerLeuSerProLysLeuThrCysLeuGln Asn LeuLysTrpSerThrAlaValGluPheCysLysLysLysSerCysProAsnProGly GluIleArgAsnGlyGlnIleAspValProGlyGlyIleLeuPheGlyAlaThrIle SerPheSerCysAsnThrGlyTyrLysLeuPheGlySerThrSerSerPheCys Leu IleSerGlySerSerValGlnTrpSerAspProLeuProGluCysArgGluIleTyr CysProAlaProProGlnIleAspAsnGlyIleIleGlnGlyGluArgAspHisTyr GlyTyrArgGlnSerValThrTyrAlaCysAsnLysGlyPheThrMetIle GlyGlu HisSerIleTyrCysThrValAsnAsnAspGluGlyGluTrpSerGlyProProPro GluCysArgGlyLysSerLeuThrSerLysValProProThrValGlnLysProThr ThrValAsnValProThrThrGluValSerProThrSerGlnLysThrThrThrLys ThrThrThrProAsnAlaGlnAlaThrArgSerThrProValSerArgThrThrLys HisPheHisGluThrThrProAsnLysGlySerGlyThrThrSerGlyThrThrArg (SEQ ID NO: 2)

MCP-DAF hybrids as used herein means polypeptides containing MCP and DAF as those terms are defined in this section. For instance, MCP-DAF hybrids may contain the entire sequence of both molecules and may contain just the SCR regions from each MCP and DAF. An example of an MCP-DAF hybrid is the molecule disclosed by Iwata et al, supra having the first 250 amino acids of MCP covalently linked to DAF. Sequences separating the MCP and DAF portions may be introduced as well. The MCP-DAF hybrid molecule may also have the following amino-acid sequence: CysGluGluProProThrPheGluAlaMetGluLeuIleGlyLysProLysProTyr TyrGluIleGlyGluArgValAspTyrLysCysLysLysGlyTyrPheTyrIlePro ProLeuAlaThrHisThrIleCysAspArgAsnHisThrTrpLeuProVal SerAsp AspAlaCysTyrArgGluThrCysProTyrIleArgAspProLeuAsnGlyGlnAla ValProAlaAsnGlyThrTyrGluPheGlyTyrGlnMetHisPheIleCysAsnGlu GlyTyrTyr- LeuIleGlyGluGluIleLeuTyrCysGluLeuLysGlySerValAla IleTrpSerGlyLysProProIleCysGluLysValLeuCysThrProProProLys IleLysAsnGlyLysHisThrPheSerGluValGluValPheGluTyrLeuAspAla ValThrTyrSerCysAspProAlaProGlyProAspProPheSerLeuIleGly Glu SerThrIleTyrCysGlyAspAsnSerValTrpSerArgAlaAlaProGluCysLys ValValLysCysArgPheProValValGluAsnGlyLysGlnIleSerGlyPheGly LysLysPheTyrTyrLysAlaThrValMetPheGluCysAspLysGlyPheTyrLeu AspGlySerAspThrIleValCysAspSerAsnSerThrTrpAspProProValPro LysCysLeuLysValSerThrAspCysGlyLeuProProAspValProAsnAlaGln ProAlaLeuGluGlyArgThrSerPheProGluAspThrValIleThrTyrLysCys GluGluSerPheValLysIleProGlyGluLysAspSerValIleCysLeuLys Gly SerGlnTrpSerAspIleGluGluPheCysAsnArgSerCysGluValProThrArg LeuAsnSerAlaSerLeuLysGlnProTyrIleThrGlnAsnTyrPheProValGly ThrValValGluTyrGluCysArgProGlyTyrArgArgGluProSerLeuSerPro LysLeuThrCysLeuGlnAsnLeuLysTrpSerThrAlaValGluPheCysLysLys LysSerCysProAsnProGlyGluIleArgAsnGlyGlnIleAspValProGlyGly IleLeuPheGlyAlaThrIleSerPheSerCysAsnThrGlyTyrLysLeuPhe Gly SerThrSerSerPheCysLeuIleSerGlySerSerValGlnTrpSerAspProLeu ProGluCysArgGluIleTyrCysProAlaProProGlnIleAspAsnGlyIleIle GlnGlyGluArgAspHisTyrGlyTyrArgGlnSerValThrTyrAlaCysAsnLys GlyPheThrMetIleGlyGluHisSerIleTyrCysThrValAsnAsnAspGluGly GluTrpSerGlyProProProGluCysArgGlyLysSerLeuThrSerLysvalPro ProThrValGlnLysProThrThrValAsnValProThrThrGluValSerProThr Ser-GlnLysThrThrThrLysThrThrThrProAsnAlaGlnAlaThrArgSerThr ProValSerArgThrThrLysHisPheHisGluThrThrProAsnLysGlySerGly ThrThrSerGlyThrThrArg (SEQ ID NO: 3).

The chimeric proteins of the invention include proteins with sequences which inhibit complement function and sequences which bind to glycosaminoglycans present on cell surfaces, particularly heparin. The sequences which inhibit complement function are MCP, DAF and MCP-DAF hybrids. These peptide sequences preferably have glycosaminoglycan binding ability and, most preferably, bind heparin. Consensus sequences capable of binding heparin have been identified by Cardin and Weintraub, *Arteriosclerosis,* (1989) 9:21–32 and by Sobel et al. (1992) *J. Biol. Chem.* 267:8857–8862. The consensus sequence can be represented as follows:

XBBXXBBBXXBBX where X represents hydropathic amino acids and B represents the basic amino acids lysine and arginine. One example of a peptide according to the consensus is Ala-Lys-Arg-Gly-Leu-Arg-Arg-Arg-Leu-Gly-Arg-Lys-Ala (SEQ ID NO: 4). A second consensus sequence can be represented by:

XBBXBX where X represents hydropathic amino acids and B represents the basic amino acids lysine and arginine. An example of this shorter sequence is Ala-Arg-Arg-Gly-Lys-Leu (SEQ ID NO: 5). Any sequence matching the two consensus sequences described may be used in the A or the C position or both to target the MCP-DAF hybrid to cell surfaces.

Two sequences derived from fibronectin can also be used as glycosaminoglycan binding sequences. The first, Trp-Gln-Pro-Pro-Arg-Ala-Arg-Ile (SEQ ID NO: 6) was identified by Woods et al., *Molec. Biol. Cell* (1993) 4:605–613. The second, Leu-Ile-Gly-Arg-Lys-Lys (SEQ ID NO: 7) was described by Drake et al., *J.Biol.Chem.,* (1993) 268:15859–15867.

Peptide sequences having glycosaminoglycan binding ability may be derived from proteins having heparin binding activity including, but not limited to, the following: protease nexin-1, protease nexin-2, antithrombin III, protein C inhibitor, platelet factor 4, heparin cofactor II, ghilanten-related inhibitors, bovine pancreatic trypsin inhibitor, tissue factor pathway inhibitor (hereinafter 'TFPI') (also known as LACI, TFI and EPI) or TFPI-2.

In the case of antithrombin III, the appropriate portion may be Ala Lys Leu Asn Cys Arg Leu Tyr Arg Lys Ala Asn Lys Ser Ser Lys Leu. (SEQ ID NO: 8). The appropriate portion of antithrombin III may also be Thr Ser Asp Gln Ile His Phe Phe Phe Ala Lys Leu Asn Cys Arg. (SEQ ID NO: 9).

In the case of protein C inhibitor, the appropriate portion may be Ser Glu Lys Thr Leu Arg Lys Trp Leu Lys Met Phe Lys Lys Arg Glu Leu Glu Glu Tyr (SEQ ID NO: 10).

The appropriate portion of protein C inhibitor may also be His Arg His His Pro Arg Glu Met Lys Lys Arg Val Glu Asp Leu (SEQ ID NO: 11).

In the case of heparin cofactor II, the appropriate portion may be Phe Arg Lys Leu Thr His Arg Leu Phe Arg Arg Asn Phe Gly Tyr Thr Leu Arg (SEQ ID NO: 12).

In the case of platelet factor 4, the appropriate portion may be Leu Tyr Lys Lys Ile Leu Lys Lys Leu Leu Glu Ala (SEQ ID NO: 13).

In the case of ghilanten-related inhibitors, the appropriate portion may be Asn Gly Leu Lys Arg Asp Lys Leu Gly Cys Glu Tyr Cys Glu Cys Arg Pro Lys Arg Lys Leu Ile Pro Arg Leu Ser (SEQ ID NO: 14).

In the case of TFPI, the appropriate portion may be Lys Thr Lys Arg Lys Arg Lys Lys Gln Arg Val Lys Ile Ala Tyr Glu Glu Ile Phe Val Lys Asn Met (SEQ ID NO: 15).

In the case of TFPI-2, the appropriate portion may be Lys Lys Lys Lys Lys Met Pro Lys Leu Arg Phe Ala Ser Arg Ile Arg Lys Ile Arg Lys Lys Gln Phe (SEQ ID NO: 16).

Those skilled in the art will appreciate that various deletions, substitutions and insertions may be made to the above-listed sequences without substantially interfering with the ability of the sequence to bind to heparin. Such modifications to the above-listed sequences should be understood to fall within the scope of the invention.

Production of Chimeric Proteins of the Invention

One skilled in the art of DNA cloning and in possession of the DNA encoding MCP, DAF, and a cell surface localizing domain is able to prepare suitable DNA molecules for production of such chimeric proteins using known cloning procedures (e.g. restriction enzyme digestion of MCP, DAF, or cell surface localizing domain encoding DNA, exonuclease digestion, ligation, and other appropriate procedures) outlined in any of the following: Sambrook, et al, MOLECULAR CLONING: A LABORATORY MANUAL 2nd ed. (Cold Spring Harbor Laboratory Press, 1989); DNA CLONING, Vol. I and II, D. N. Glover ed. (IRL Press, 1985); OLIGONUCLEOTIDE SYNTHESIS, M. J. Gait ed. (IRL Press, 1984); NUCLEIC ACID HYBRIDIZATION, B. D. Hames & S. J. Higgins eds. (IRL Press, 1984); TRANSCRIPTION AND TRANSLATION, B. D. Hames & S. J. Higgins eds., (IRL Press, 1984); ANIMAL CELL CULTURE, R. I. Freshney ed. (IRL Press, 1986); IMMOBILIZED CELLS AND ENZYMES, K. Mosbach (IRL Press, 1986); B. Perbal, A PRACTICAL GUIDE TO MOLECULAR CLONING, Wiley (1984); the series, METHODS IN ENZYMOLOGY, Academic Press, Inc.; GENE TRANSFER VECTORS FOR MAMMALIAN CELLS, J. H. Miller and M. P. Calos eds. (Cold Spring Harbor Laboratory, 1987); METHODS IN ENZYMOLOGY, Vol. 154 and 155, Wu and Grossman, eds., and Wu, ed., respectively (Academic Press, 1987), IMMUNOCHEMICAL METHODS IN CELL AND MOLECULAR BIOLOGY, R. J. Mayer and J. H. Walker, eds. (Academic Press London, Harcourt Brace U.S., 1987), PROTEIN PURIFICATION: PRINCIPLES AND PRACTICE, 2nd ed. (Springer-Verlag, N.Y. (1987), and HANDBOOK OF EXPERIMENTAL IMMUNOLOGY, Vol. I–IV, D. M. Weir et al, (Blackwell Scientific Publications, 1986); Kitts et al, *Biotechniques,* (1993), 14:810–817; Munemitsu et al, *Mol. Cell. Biol.,* (1990) 10:5977–5982. Alternatively, the entire sequence or portions of nucleic acid sequences encoding proteins described above may be prepared by synthetic methods (e.g. using DNA synthesis machines). Finally, a preferred method of preparing nucleic acid molecules encoding the described chimeric proteins is by use of PCR techniques, especially overlapping PCR, as described in PCR PROTOCOLS: A GUIDE TO METHODS AND APPLICATIONS, Innis, Gelfand, Sninsky, and White (eds.) (Academic Press, 1990).

The proteins described above may be prepared using any suitable expression system including, without limitation, the following expression systems: mammalian tissue culture, insect cell culture, bacterial cell culture and yeast cell culture. It will be understood that the proteins of the invention may be within the cells as precursor molecules which may be cleaved within the cells to produce the desired protein. Alternatively, the precursor proteins may be recovered from the cells and further processed to recover the desired protein. Mammalian expression systems are known in the art. Sambrook et al "Expression of Cloned Genes in Mammalian Cells." In MOLECULAR CLONING: A LABORATORY MANUAL 2nd ed. (Cold Spring Harbor Laboratory Press, 1989). Mammalian cell lines available as hosts for expression are known in the art and include many immortalized cell lines available from the American Type Culture Collection (ATCC).

The proteins of the invention may also be produced in insect cells using a vector containing baculovirus sequences. Materials and methods for baculovirus/insect cell expression systems are commercially available in kit form from, inter alia, Invitrogen, San Diego Calif. ("MaxBac" kit). These techniques are generally known to those skilled in the art and fully described in Summers and Smith, Texas Agricultural Experiment Station Bulletin No. 1555 (1987) (hereinafter "Summers and Smith"). Currently, the most commonly used transfer vector for introducing foreign genes into AcNPV is pAc373. Many other vectors, known to those of skill in the art, have also been designed. These include, for example, pVL985 (which alters the polyhedrin start codon from ATG to ATT, and which introduces a BamHI cloning site 32 base pairs downstream from the ATT; see Luckow and Summers, *Virology* (1989) 17:31. Methods for introducing heterologous DNA into the desired site in the baculovirus virus are known in the art. (See Summers and Smith, supra; Ju et al (1987); Smith et al, *Mol. Cell. Biol.,* (1983) 3:2156; and Luckow and Summers (1989), supra). For example, the insertion can be into a gene such as the polyhedrin gene, by homologous double crossover recombination; insertion can also be into a restriction enzyme site engineered into the desired baculovirus gene. Miller et al, *Bioessays* (1989) 4:91. The DNA sequence, when cloned in place of the polyhedrin gene in the expression vector, is flanked both 5' and 3' by polyhedrin-specific sequences and is positioned downstream of the polyhedrin promoter.

Recombinant baculovirus expression vectors have been developed for infection into several insect cells. For example, recombinant baculoviruses have been developed for, inter alia: *Aedes aegypti, Bombyx mori, Drosophila melanogaster, Spodopterafrugiperda,* and *Trichoplusia ni* (PCT Pub. No. WO 89/046699; Carbonell et al, *J. Virol.* (1985) 56:153; Wright, *Nature* (1986) 321:718; Smith et al, *Mol. Cell. Biol.,* (1983) 3:2156; and see generally, Fraser, et al *Cell. Dev. Biol.,* (1989) 25:225. Cells and cell culture media are commercially available for both direct and fusion expression of heterologous polypeptides in a baculovirus/expression system; cell culture technology is generally known to those skilled in the art. See, e.g., Summers and Smith, supra. The modified insect cells may then be grown in an appropriate nutrient medium, which allows for stable maintenance of the plasmid(s) present in the modified insect host. One such nutrient medium is described in EP 380 495.

Numerous bacterial expression techniques are known in the art. Sambrook et al "Expression of cloned genes in *Escherichia coli.*" In MOLECULAR CLONING: A LABORATORY MANUAL 2nd ed. (Cold Spring Harbor Laboratory Press, 1989).

Expression and transformation vectors, either extrachromosomal replicons or integrating vectors, have been developed for transformation into many bacteria. For example, expression vectors have been developed for, inter alia, the following bacteria: *Bacillus subtilis* (Palva et al, *Proc. Natl. Acad. Sci. USA,* (1982) 79:5582; EP 036 259 and 063 953; PCT WO 84/04541), *E. coli* (Shimatake et al., *Nature*, (1981) 292:128; Amann et al, *Gene* (1985) 40:183; Studier et al, *J. Mol. Biol.,* (1986) 189:113; EP Publ. Nos. 036 776, 136 829 and 136 907), *Streptococcus cremoris* (Powell et al., *Appl. Environ. Microbiol.,* (1988) 54:655); *Streptococcus lividans* (Powell et al., Appl. Environ. Microbiol., (1988) 54:655), *Streptomyces lividans* (U.S. Pat. No. 4,745,056).

The DNA encoding the protein of the present invention may be joined to a signal peptide for export or secretion of the mature protein to the periplasmic space of bacteria, using techniques that are conventional in the art. Moreover, transcription and translation can further be optimized in a bacterial expression system by varying the spacing between the DNA to be expressed and the sequences encoding the promoter and ribosome binding site.

Yeast expression systems are also known in the art. Fusion proteins provide one means for expression of the proteins of the invention in yeast systems. Usually, a DNA sequence encoding the N-terminal portion of an endogenous yeast protein, or other stable protein, is fused to the 5' end of a heterologous coding sequence. Upon expression, this construct will provide a fusion of the two amino acid sequences. The DNA sequence at the junction of the two amino acid sequences may or may not encode a cleavable site. See e.g., EP 196 056. One such fusion protein is a ubiquitin fusion protein. Such a fusion protein is made with the ubiquitin region that may retain a site for a processing enzyme, which allows a ubiquitin-specific processing protease to cleave the ubiquitin from the foreign protein. Through this method, therefore, foreign protein with an authentic amino terminus can be isolated from within the yeast cell. Production of ubiquitin fusion proteins is described in co-pending U.S. Patent Application Ser. Nos. 07/806,813, now abandoned and 07/957,627 now abandoned. This method is reviewed in Barr et al, in RECOMBINANT SYSTEMS IN PROTEIN EXPRESSION (Elsevier Science Publishers B. V., 1991), pp. 37–46.

Alternatively, foreign proteins can be secreted from the cell into the growth media by creating chimeric DNA molecules that encode a fusion protein comprised of a leader sequence fragment that provide for secretion in yeast of the foreign protein. There may be processing sites encoded between the leader fragment and the foreign gene that can be cleaved either in vivo or in vitro. The leader sequence fragment usually encodes a signal peptide comprised of hydrophobic amino acids which direct the secretion of the protein from the cell.

DNA encoding suitable signal sequences can be derived from genes for secreted yeast proteins, such as the yeast invertase gene (EP 012 873; JPO 62,096,086), the α-factor gene (U.S. Pat. Nos. 4,588,684 and 4,870,008; EP 116,201) and truncated versions of the α-factor gene as described in EP 324 274 and co-pending U.S. patent application Ser. No. 07/864,206 now abandoned. Alternatively, leaders of non-yeast origin, such as an interferon leader, exist that also provide for secretion in yeast (EP 060 057). The α-factor gene may be used in nucleic acid constructs designed for secretion of the proteins of the invention.

Another useful class of secretion leaders are those that employ a fragment of the yeast α-factor gene, which contains both a "pre" signal sequence, and a "pro" region. The types of α-factor fragments that can be employed include the full-length pre-pro α-factor leader (about 83 amino acid residues) as well as truncated α-factor leaders (usually about 25 to about 50 amino acid residues) (U.S. Pat. Nos. 4,546,083 and 4,870,008; EP 324 274). Additional leaders employing an α-factor leader fragment that provides for secretion include hybrid α-factor leaders made with a presequence of a first yeast, but a pro-region from a second yeast α-factor. (See e.g., PCT WO 89/02463.)

Expression vectors encoding the proteins of the invention are often maintained in a replicon, such as an extrachromosomal element (e.g., plasmid) capable of stable maintenance in a host, such as yeast or bacteria. The replicon may have two replication systems, thus allowing it to be maintained, for example, in yeast for expression and in a procaryotic host for cloning and amplification. Examples of such yeast-bacteria shuttle vectors include YEp24 (Botstein et al, *Gene,* (1979) 8:17–24), pCl/1 (Brake et al, *Proc. Natl. Acad. Sci USA,* (1984) 81:4642–4646), and YRp17 (Stinchcomb et al, *J. Mol. Biol.,* (1982) 158:157). In addition, a replicon may be either a high or low copy number plasmid. A high copy number plasmid will generally have a copy number ranging from about 5 to about 200, and usually about 10 to about 150. A host containing a high copy number plasmid will may have at least about 10, and may have at least about 20. Either a high or low copy number vector may be selected, depending upon the effect of the vector and the foreign protein on the host. See e.g., Brake et al, supra. For production of the proteins of the invention in a yeast cell wherein the protein is retained within the yeast cell, a plasmid such as pAB24 may be used. Sabin et al, *Bio/Technology,* (1989) 7:705–709. pAB24 contains a GAP/ADH hybrid promoter, containing portions of an ADH promoter capable of directing high levels of expression of the sequences under its control but which also contains GAP regulatory sequences, allowing expression of the same sequence a desired point in the growth of a culture.

Alternatively, the expression constructs can be integrated into the host genome with an integrating vector. Integrating vectors usually contain at least one sequence homologous to a host chromosome that allows the vector to integrate, and may contain two homologous sequences flanking the expression construct. Integrations appear to result from recombinations between homologous DNA in the vector and the host chromosome. Orr-Weaver et al, *Meth. Enzymol.,* (1983) 101:228–245. An integrating vector may be directed to a specific locus in yeast by selecting the appropriate homologous sequence for inclusion in the vector. See Orr-Weaver et al, supra. One or more expression construct may integrate, possibly affecting levels of recombinant protein produced. Rine et al, *Proc. Natl. Acad. Sci. USA,* (1983) 80:6750. The chromosomal sequences included in the vector can occur either as a single segment in the vector, which results in the integration of the entire vector, or two segments homologous to adjacent segments in the chromosome and flanking the expression construct in the vector, which can result in the stable integration of only the expression construct.

Usually, extrachromosomal and integrating expression constructs may contain selectable markers to allow for the selection of yeast strains that have been transformed. Selectable markers may include biosynthetic genes that can be expressed in the yeast host, such as ADE2, HIS4, LEU2, TRP1, and ALG7, and the G418 resistance gene, which confer resistance in yeast cells to tunicamycin and G418, respectively. In addition, a suitable selectable marker may also provide yeast with the ability to grow in the presence of toxic compounds, such as metal. For example, the presence of CUP1 allows yeast to grow in the presence of copper ions (Butt et al, *Microbiol. Rev.* (1987) 51:351).

Alternatively, some of the above described components can be put together into transformation vectors. Transformation vectors are usually comprised of a selectable marker that is either maintained in a replicon or developed into an integrating vector, as described above.

Expression and transformation vectors, either extrachromosomal replicons or integrating vectors, have been developed for transformation into many yeasts. For example, expression vectors have been developed for, inter alia, the following yeasts: *Candida albicans* (Kurtz, et al, *Mol. Cell. Biol.,* (1986) 6:142), *Candida maltosa* (Kunze, et al, *J. Basic Microbiol.,* (1985) 25:141), *Hansenula polymorpha* (Gleeson, et al, *J. Gen. Microbiol.,* (1986) 132:3459; Roggenkamp et al, *Mol. Gen. Genet.,* (1986) 202:302), *Kluyveromyces fragilis* (Das, et al, *J. Bacteriol.,* (1984) 158:1165), *Kluyveromyces lactis* (De Louvencourt et al, *J. Bacteriol.,* (1983) 154:737; Van den Berg et al, *Bio/Technology,* (1990) 8:135), *Pichia guillerimondii* (Kunze et al, *J. Basic Microbiol.,* (1985) 25:141), *Pichia pastoris* (Cregg, et al, *Mol. Cell. Biol.,* (1985) 5:3376; U.S. Pat. Nos. 4,837,148 and 4,929,555), *Saccharomyces cerevisiae* (Hinnen et al, *Proc. Natl. Acad. Sci. USA,* (1978) 75:1929; Ito et al, *J. Bacteriol.,* (1983) 153:163), *Schizosaccharomyces pombe* (Beach and Nurse, *Nature,* (1981) 300:706), and *Yarrowia lipolytica* (Davidow, et al, *Curr. Genet.* (1985) 10:380471 and Gaillardin et al, *Curr. Genet.,* (1985) 10:49).

Transformation procedures that may be used herein to transform yeast cells include electroporation, as described in "Guide to Yeast Genetics and Molecular Biology," Vol 194 METHODS IN ENZYMOLOGY, C. Guthrie and G. R. Fink, (Academic Press 1991). Other procedures include the transformation of spheroplasts or the transformation of alkali cation-treated intact cells. Such procedures are described in, for example, Kurtz et al, *Mol. Cell. Biol.,* (1986) 6:142; Kunze et al, *J. Basic Microbiol.,* (1985) 25:141, for Candida; Gleeson et al, *J. Gen. Microbiol.,* (1986) 132:3459; Roggenkamp et al., *Mol. Gen. Genet.,* (1986) 202:302, for Hansenula; Das et al, *J. Bacteriol.* (1984) 158:1165; De Louvencourt et al, *J. Bacteriol.,* (1983) 154:1165; Van den Berg et al, *Bio/Technology,* (1990) 8:135 for Kluyveromyces; Cregg et al, *Mol. Cell. Biol.* 5:3376

(1985); Kunze et al, *J. Basic Microbiol.,* (1985) 25:141; U.S. Pat. Nos. 4,837,148 and 4,929,555, for Pichia; Hinnen et al, *Proc. Natl. Acad. Sci. USA,* (1978) 75:1929; Ito et al, *J. Bacteriol.,* (1983) 153:163, for Saccharomyces; Beach and Nurse, *Nature,* (1981) 300:706, for Schizosaccharomyces; Davidow et al, *Curr. Genet.,* (1985) 10:39; Gaillardin et al, *Curr. Genet.,* (1985) 10:49, for Yarrowia.

The present invention will now be illustrated by reference to the following examples which set forth particularly advantageous embodiments. However, it should be noted that these embodiments are illustrative and are not to be construed as restriction in any way.

EXAMPLES

Example 1

A chimeric protein according to the invention is constructed comprising the protein (SEQ ID NO: 3), an MCP-DAF hybrid molecule with the following amino acid sequence attached to the carboxy-terminal end of the MCP-DAF hybrid molecule: Ala-Lys-Arg-Gly-Leu-Arg-Arg-Arg-Leu-Gly-Arg-Lys-Ala (SEQ ID NO: 4). The chimeric protein is constructed using overlapping PCR. The DNA used as the PCR template is (SEQ ID NO: 17) which encodes the MCP-DAF hybrid (SEQ ID NO: 3) along with the MCP signal peptide. The following primer will be used as the 3' end primer to introduce (SEQ ID NO: 4) to the carboxy-terminal end of the MCP-DAF hybrid molecule:

CAGAGAATTCTCAAGCTTTTCTAC-CTAGTCTTCTTCTTAGACCTC TTTTAGCTCGGGTAGTAC-CTGAAGTGGT (SEQ ID NO: 18).

The 5' end primer will be:

CAGAGGTACCATGGAGCCTCCCGGCCGCCGC (SEQ ID NO: 19).

The 5' end primer has a KpnI and the 3' end primer has an EcoRI site to direct the cloning of the resulting DNA in predigested pAcC13, a plasmid containing baculovirus sequences allowing expression of the DNA in insect cells as described above. A pAcC13 vector containing a PR-3 sequence and useable in the present example has been deposited with the A.T.C.C. as described below. Those skilled in the art will appreciate that the insert present in the deposited plasmid can be removed by methods known in the art.

Alternatively, a shorter heparin binding sequence, Ala-Arg-Arg-Gly-Lys-Leu (SEQ ID NO: 5), can be added to the carboxy-terminal end of the MCP-DAF hybrid (SEQ ID NO: 3). In this case the primer will be:

CAGAGAATTCTCATAGTTTACCTCT-TCTAGCTCGGGTAGTACCT GAAGTGGT (SEQ ID NO: 20).

As before, the 3' end primer has an EcoRI site to direct the cloning of the resulting DNA into pAcC13.

Example 2

The heparin binding tail of TFPI can also be used in construction of the chimeric proteins of the invention. In this case, the heparin binding tail Lys-Thr-Lys-Arg-Lys-Arg-Lys-Lys-Gln-Arg-Val-Lys-Ile-Ala-Tyr-Glu-Glu-Ile-Phe-Val-Lys-Asn-Met. (SEQ ID NO: 15) is attached to the carboxy-terminal end of the MCP-DAF hybrid (SEQ ID NO: 3). As in Example 1, the DNA encoding the MCP-DAF hybrid along with the MCP signal peptide (SEQ ID NO: 17) is used as the template for overlapping PCR and the 5' end primer is again (SEQ ID NO: 19). The 3' end primer has the nucleotide sequence:

CAGAGAATTCTCACATATTTTTAA-CAAAAATTTCTTCATATGCT ATTTTCACTCTCTGCT-TCTTTCTTTTTCTTTTGGTTTTTCGGGTAGTACCT GAAGTGGT (SEQ ID NO: 21).

The 3' end primer has an EcoRI site allowing directed cloning of the resulting PCR products into pAcC13 for transformation into and expression in insect cells.

Alternatively, the PCR is run in two rounds using the following 5' primer:

ACTTCAGGTACTACCCGTAAAACCAAAAGA (SEQ ID NO: 22)

and the following 3' end primer:

TGAAGTCCATGATGGGCATTTTGGTTTTCTTTTTCT (SEQ ID NO: 23).

To introduce the EcoRI site, a second round of PCR is performed using the same 5' end primer and a 3' end primer having the following sequence:

CAGAGAATTCTCACATATTTTTAACAAAAATTTC (SEQ ID NO: 24).

Example 3

In this example, the fibronectin derived sequence Trp-Gln-Pro-Pro-Arg-Ala-Arg-Ile (SEQ ID NO: 6) is attached to the MCP-DAF hybrid (SEQ ID NO: 3). PCR is performed using the 5' end primer (SEQ ID NO: 19) and the 3' primer having the following sequence:

CAGAGAATTCTCATATTCTAGCTCTAG-GAGGCTGCCATCGGGTA GTACCTGAAGTGGT (SEQ ID NO: 25).

The 5' end primer has a KpnI and the 3' end primer has an EcoRI site to direct the cloning of the resulting DNA in predigested pAcC13, a plasmid containing baculovirus sequences allowing expression of the DNA in insect cells as described above.

Example 4

Another fibronectin sequence is also useful for constructing chimeric proteins according to the invention. The amino acid sequence is Leu-Ile-Gly-Arg-Lys-Lys (SEQ ID NO: 7) and is attached to the carboxy-terminal end of the MCP-DAF hybrid (SEQ ID NO: 3). PCR is performed using the 5' end primer (SEQ ID NO: 19) and the 3' primer having the following sequence:

CAGAGAATTCTCAGGTTTTTTTTCTAC-CTATTAGTCGGGTAGTAC CTGAAGTGGT (SEQ ID NO: 26).

The 5' end primer has a KpnI and the 3' end primer has an EcoRI site to direct the cloning of the resulting DNA in predigested pAcC13, a plasmid containing baculovirus sequences allowing expression of the DNA in insect cells as described above.

Example 5

Assay for Complement Inhibiting Activity of Chimeric Proteins of the Invention

Inhibition of Classical Pathway Activation

Human serum is diluted in Gelatin Veronal Buffer (GVB) (Sigma, St. Louis, Mo. Catalog #G-6514) to yield sufficient complement to effect 70% maximum hemolysis. Dilutions may range from 1:10 to 1:120. IgM-sensitized sheep red blood cell (SRBC) suspension (Diamedix CH50 Test Kit #789-001) is transferred to a centrifuge tube and spun at 500×g for 1 minute (2 to 8 degrees C.). Two ml of the supernatant liquid is removed and the SRBC are resuspended in the remaining 1 ml. This preparation is then stored in an ice water bath.

The following are then added to duplicate wells of a V-bottom microtiter plate:

Experimentals containing 100 μl SRBC suspension; 50 ul GVB; 50 ul each serum dilution Negative control containing 100 μl SRBC suspension; 100 μl GVB Maximum lysis control containing 100 μl of SRBC suspension which has been spun down as above and resuspended in 200 μl of water The plate is incubated at 37 degrees C. for 30 minutes. The plates are then subjected to centrifugation at 500×g for 1 minute (2 to 8 degrees C.) and 100 ul of the resulting supernatant liquid is drawn off. The absorbance of each sample is then measured at 405 nm. Percent maximum lysis for each serum dilution is then calculated according to the formula:

{[O.D.sample-O.D.neg.control]/[O.D.maximum-O.D.neg.control]}×100.

The serum dilution at which approximately 70% maximum lysis occurs is the dilution at which subsequent assays with the molecules of the invention should be performed. This dilution will apply only to the specific lot of human serum tested and must be repeated for each new serum lot Standard solutions containing the molecules of the invention may be prepared in GVB at a concentration of 0.8 μM for dilution. (This concentration may be adjusted up or down, depending on the activity of the particular molecule). Standards using MCP or MCP-DAF may be formulated using 80 μM MCP or 0.8 μM MCP-DAF. Four serial 1:2 dilutions of the standard solution are prepared. The assays are then conducted by adding the following components to duplicate wells of a V-bottom microtiter plate:

Experimentals 100 μl SRBC suspension; 50 μl standard solution or dilution; 50 μl of serum dilution Negative control 100 μl SRBC suspension; 50 μl standard solution; 50 μl GVB Positive control 100 μl SRBC suspension which has been spun down as above and resuspended in 200 μl of water The plate is incubated at 37 degrees C. for 30 minutes. The plates are then subjected to centrifugation at 500×g for 1 minute (2 to 8 degrees C.) and 100 μl of the resulting supernatant liquid is drawn off. The absorbance of each sample is then measured at 405 nm. Percent positive control SRBC lysis for each dilution is then calculated according to the formula:

{[O.D.sample-O.D.neg.control]/[O.D.pos.control-O.D.neg.control]}×100.

The % inhibition is 100% −(% positive control).

Factor I Assay

Standards are prepared by dilution of the molecules of the invention into 20 μl of Assay Buffer (3 mM sodium phosphate, pH 7.2; 25 mM sodium chloride; 0.5% NP-40) to a concentration of approximately 6.0 nM. Five serial 1:2 dilutions are then prepared. For each assay 6 ul of the serial dilutions are added to 2 μl of Factor I solution and 8 μl of iC3 solution. Factor I Stock Solution is prepared using 1 mg Factor I (Quidel, catalog #A411) in 1 ml Assay Buffer. Immediately before use, 4 ul of Factor I Stock Solution is added to 50 μl Assay Buffer to prepare the Factor I solution. iC3 solution is prepared using 0.5 mg purified C3 (Quidel, catalog #A401) in 1 ml Assay Buffer. An equal amount of 4.0M potassium bromide is added and the iC3 Solution is incubated at 37 degrees C. for 1 hour, protecting the mixture from light.

Negative controls are also prepared using: 8 μl iC3 solution, 6 μl Assay Buffer and 2 μl Factor I solution. The samples are then incubated for 1 hour at 37 degrees C. The reactions are stopped by addition of SDS Sample Buffer (20% sucrose; 2% sodium dodecyl sulfate; 100 mM Tris, pH 6.8; 20 mM dithiothreitol; 0.01% bromphenol blue) to each tube. The samples are then boiled in a 100 degree water bath for five minutes and allowed to cool to room temperature. The samples are then subjected to electrophoresis on a 10% polyacrylamide gel. The gel is stained for 1 hour in 50% methanol; 10% acetic acid; 0.05% Coomassie Brilliant Blue. The gel may then be destained overnight in 15% methanol and 10% acetic acid. The gel is dried and the lanes of the gel may be scanned using a densitometer. The C3α chain has a native molecular weight of 120 kD and is cleaved into 75kD and 45kD fragments. The area under the three peaks corresponding to each complement component is determined and the percentage of the total area each peak represents is calculated. The percentage cleavage of the alpha chain is calculated as follows:

% cleavage=100% −(% of total area which is native mw).

Deposit Information

The following materials were deposited with the American Type Culture Collection:

| Plasmid | Deposit Date | Accession No. |
|---|---|---|
| pAcC13preproPR-3 | January 27, 1994 | 69542 |

The above materials were deposited by Chiron Corporation, an assignee of the present invention with the American Type Culture Collection (ATCC), 12301 Parklawn Drive, Rockville, Md. under the terms of the Budapest Treaty on the International Recognition of the Deposit of Microorganisms for purposes of Patent Procedure. The accession number is available from the ATCC at telephone number (301) 881–2600.

These deposits are provided as convenience to those of skill in the art, and are not an admission that a deposit is required under 35 U.S.C. §112. The nucleic acid sequence of any of these deposits, as well as the amino acid sequence of the polypeptides encoded thereby, are incorporated herein by reference and should be referred to in the event of an error in the sequence described herein. A license may be required to make, use, or sell the deposited materials, and no such license is granted hereby.

We claim:

1. A chimeric protein comprising a) a hybrid comprising a membrane co-factor protein (MCP) portion linked to a decay accelerating factor (DAF) portion, wherein each portion has complement inhibitory activity, and b) a tissue factor pathway inhibitor (TFPI) peptide, which peptide has glycosaminoglycan binding ability, attached to the amino-terminal end or the carboxy-terminal end of the hybrid.

2. The chimeric protein of claim 1, further comprising a peptide separating the MCP and DAF portions of the hybrid.

3. The chimeric protein of claim 1, wherein the MCP portion is attached to the amino-terminal end of the DAF portion.

4. The chimeric protein of claim 1, wherein the TFPI peptide is attached to the carboxy-terminal end of the hybrid.

5. The chimeric protein of claim 1, wherein the TFPI peptide is SEQ ID NO:15.

6. A nucleic acid comprising a nucleotide sequence encoding a chimeric protein comprising a) a hybrid comprising an MCP portion linked to a DAF portion, wherein each portion has complement inhibitory activity, and b) a TFPI peptide, which peptide has glycosaminoglycan binding ability, attached to the amino-terminal or the carboxy-terminal end of the hybrid.

7. The nucleic acid of claim 6, wherein the chimeric protein further comprises a peptide separating the MCP and DAF portions of the hybrid.

8. The nucleic acid of claim 6, wherein the MCP portion of the chimeric protein is attached to the amino-terminal end of the DAF portion.

9. The nucleic acid of claim 6, wherein the TFPI peptide of the chimeric protein is attached to the carboxy-terminal end of the hybrid.

10. The nucleic acid of claim 6, wherein the TFPI peptide of the chimeric protein is SEQ ID NO:15.

11. A transformed host cell containing a nucleic acid, wherein the nucleic acid comprises a nucleotide sequence encoding a chimeric protein comprising a) a hybrid comprising an MCP portion linked to a DAF portion, wherein each portion has complement inhibitory activity, and b) a TFPI peptide, which peptide has glycosaminoglycan binding ability, attached to the amino-terminal or the carboxy-terminal end of the hybrid.

12. The transformed host cell of claim 11, wherein the chimeric protein further comprises a peptide separating the MCP and DAF portions of the hybrid.

13. The transformed host cell of claim 11, wherein the MCP portion of the chimeric protein is attached to the amino-terminal end of the DAF portion.

14. The transformed host cell of claim 11, wherein the TFPI peptide of the chimeric protein is attached to the carboxy-terminal end of the hybrid.

15. The transformed host cell of claim 11, wherein the TFPI peptide of the chimeric protein is SEQ ID NO:15.

* * * * *

SEQUENCE LISTING ( 1 ) GENERAL INFORMATION:

( i i i ) NUMBER OF SEQUENCES: 26

( 2 ) INFORMATION FOR SEQ ID NO:1:

( i ) SEQUENCE CHARACTERISTICS:
( A ) LENGTH: 254 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:1:

```
Cys Glu Glu Pro Pro Thr Phe Glu Ala Met Glu Leu Ile Gly Lys Pro
1               5                   10                  15

Lys Pro Tyr Tyr Glu Ile Gly Glu Arg Val Asp Tyr Lys Cys Lys Lys
            20                  25                  30

Gly Tyr Phe Tyr Ile Pro Pro Leu Ala Thr His Thr Ile Cys Asp Arg
        35                  40                  45

Asn His Thr Trp Leu Pro Val Ser Asp Asp Ala Cys Tyr Arg Glu Thr
    50                  55                  60

Cys Pro Tyr Ile Arg Asp Pro Leu Asn Gly Gln Ala Val Pro Ala Asn
65                  70                  75                  80

Gly Thr Tyr Glu Phe Gly Tyr Gln Met His Phe Ile Cys Asn Glu Gly
                85                  90                  95

Tyr Tyr Leu Ile Gly Glu Glu Ile Leu Tyr Cys Glu Leu Lys Gly Ser
            100                 105                 110

Val Ala Ile Trp Ser Gly Lys Pro Pro Ile Cys Glu Lys Val Leu Cys
        115                 120                 125

Thr Pro Pro Pro Lys Ile Lys Asn Gly Lys His Thr Phe Ser Glu Val
    130                 135                 140

Glu Val Phe Glu Tyr Leu Asp Ala Val Thr Tyr Ser Cys Asp Pro Ala
145                 150                 155                 160

Pro Gly Pro Asp Pro Phe Ser Leu Ile Gly Glu Ser Thr Ile Tyr Cys
                165                 170                 175

Gly Asp Asn Ser Val Trp Ser Arg Ala Ala Pro Glu Cys Lys Val Val
            180                 185                 190

Lys Cys Arg Phe Pro Val Val Glu Asn Gly Lys Gln Ile Ser Gly Phe
        195                 200                 205

Gly Lys Lys Phe Tyr Tyr Lys Ala Thr Val Met Phe Glu Cys Asp Lys
    210                 215                 220

Gly Phe Tyr Leu Asp Gly Ser Asp Thr Ile Val Cys Asp Ser Asn Ser
225                 230                 235                 240

Thr Trp Asp Pro Pro Val Pro Lys Cys Leu Lys Val Ser Thr
                245                 250
```

( 2 ) INFORMATION FOR SEQ ID NO:2:

( i ) SEQUENCE CHARACTERISTICS:
( A ) LENGTH: 323 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:2:

-continued

```
Asp Cys Gly Leu Pro Pro Asp Val Pro Asn Ala Gln Pro Ala Leu Glu
1               5                   10                  15

Gly Arg Thr Ser Phe Pro Glu Asp Thr Val Ile Thr Tyr Lys Cys Glu
            20                  25                  30

Glu Ser Phe Val Lys Ile Pro Gly Glu Lys Asp Ser Val Ile Cys Leu
        35                  40                  45

Lys Gly Ser Gln Trp Ser Asp Ile Glu Glu Phe Cys Asn Arg Ser Cys
    50                  55                  60

Glu Val Pro Thr Arg Leu Asn Ser Ala Ser Leu Lys Gln Pro Tyr Ile
65                  70                  75                  80

Thr Gln Asn Tyr Phe Pro Val Gly Thr Val Val Glu Tyr Glu Cys Arg
                85                  90                  95

Pro Gly Tyr Arg Arg Glu Pro Ser Leu Ser Pro Lys Leu Thr Cys Leu
            100                 105                 110

Gln Asn Leu Lys Trp Ser Thr Ala Val Glu Phe Cys Lys Lys Lys Ser
        115                 120                 125

Cys Pro Asn Pro Gly Glu Ile Arg Asn Gly Gln Ile Asp Val Pro Gly
    130                 135                 140

Gly Ile Leu Phe Gly Ala Thr Ile Ser Phe Ser Cys Asn Thr Gly Tyr
145                 150                 155                 160

Lys Leu Phe Gly Ser Thr Ser Ser Phe Cys Leu Ile Ser Gly Ser Ser
                165                 170                 175

Val Gln Trp Ser Asp Pro Leu Pro Glu Cys Arg Glu Ile Tyr Cys Pro
            180                 185                 190

Ala Pro Pro Gln Ile Asp Asn Gly Ile Ile Gln Gly Glu Arg Asp His
        195                 200                 205

Tyr Gly Tyr Arg Gln Ser Val Thr Tyr Ala Cys Asn Lys Gly Phe Thr
    210                 215                 220

Met Ile Gly Glu His Ser Ile Tyr Cys Thr Val Asn Asn Asp Glu Gly
225                 230                 235                 240

Glu Trp Ser Gly Pro Pro Pro Glu Cys Arg Gly Lys Ser Leu Thr Ser
                245                 250                 255

Lys Val Pro Pro Thr Val Gln Lys Pro Thr Thr Val Asn Val Pro Thr
            260                 265                 270

Thr Glu Val Ser Pro Thr Ser Gln Lys Thr Thr Thr Lys Thr Thr Thr
        275                 280                 285

Pro Asn Ala Gln Ala Thr Arg Ser Thr Pro Val Ser Arg Thr Thr Lys
    290                 295                 300

His Phe His Glu Thr Thr Pro Asn Lys Gly Ser Gly Thr Thr Ser Gly
305                 310                 315                 320

Thr Thr Arg
```

( 2 ) INFORMATION FOR SEQ ID NO:3:

( i ) SEQUENCE CHARACTERISTICS:
( A ) LENGTH: 577 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:3:

```
Cys Glu Glu Pro Pro Thr Phe Glu Ala Met Glu Leu Ile Gly Lys Pro
1               5                   10                  15

Lys Pro Tyr Tyr Glu Ile Gly Glu Arg Val Asp Tyr Lys Cys Lys Lys
```

-continued 20 25 30

Gly Tyr Phe Tyr Ile Pro Pro Leu Ala Thr His Thr Ile Cys Asp Arg
35 40 45

Asn His Thr Trp Leu Pro Val Ser Asp Asp Ala Cys Tyr Arg Glu Thr
50 55 60

Cys Pro Tyr Ile Arg Asp Pro Leu Asn Gly Gln Ala Val Pro Ala Asn
65 70 75 80

Gly Thr Tyr Glu Phe Gly Tyr Gln Met His Phe Ile Cys Asn Glu Gly
85 90 95

Tyr Tyr Leu Ile Gly Glu Glu Ile Leu Tyr Cys Glu Leu Lys Gly Ser
100 105 110

Val Ala Ile Trp Ser Gly Lys Pro Pro Ile Cys Glu Lys Val Leu Cys
115 120 125

Thr Pro Pro Pro Lys Ile Lys Asn Gly Lys His Thr Phe Ser Glu Val
130 135 140

Glu Val Phe Glu Tyr Leu Asp Ala Val Thr Tyr Ser Cys Asp Pro Ala
145 150 155 160

Pro Gly Pro Asp Pro Phe Ser Leu Ile Gly Glu Ser Thr Ile Tyr Cys
165 170 175

Gly Asp Asn Ser Val Trp Ser Arg Ala Ala Pro Glu Cys Lys Val Val
180 185 190

Lys Cys Arg Phe Pro Val Val Glu Asn Gly Lys Gln Ile Ser Gly Phe
195 200 205

Gly Lys Lys Phe Tyr Tyr Lys Ala Thr Val Met Phe Glu Cys Asp Lys
210 215 220

Gly Phe Tyr Leu Asp Gly Ser Asp Thr Ile Val Cys Asp Ser Asn Ser
225 230 235 240

Thr Trp Asp Pro Pro Val Pro Lys Cys Leu Lys Val Ser Thr Asp Cys
245 250 255

Gly Leu Pro Pro Asp Val Pro Asn Ala Gln Pro Ala Leu Glu Gly Arg
260 265 270

Thr Ser Phe Pro Glu Asp Thr Val Ile Thr Tyr Lys Cys Glu Glu Ser
275 280 285

Phe Val Lys Ile Pro Gly Glu Lys Asp Ser Val Ile Cys Leu Lys Gly
290 295 300

Ser Gln Trp Ser Asp Ile Glu Glu Phe Cys Asn Arg Ser Cys Glu Val
305 310 315 320

Pro Thr Arg Leu Asn Ser Ala Ser Leu Lys Gln Pro Tyr Ile Thr Gln
325 330 335

Asn Tyr Phe Pro Val Gly Thr Val Val Glu Tyr Glu Cys Arg Pro Gly
340 345 350

Tyr Arg Arg Glu Pro Ser Leu Ser Pro Lys Leu Thr Cys Leu Gln Asn
355 360 365

Leu Lys Trp Ser Thr Ala Val Glu Phe Cys Lys Lys Lys Ser Cys Pro
370 375 380

Asn Pro Gly Glu Ile Arg Asn Gly Gln Ile Asp Val Pro Gly Gly Ile
385 390 395 400

Leu Phe Gly Ala Thr Ile Ser Phe Ser Cys Asn Thr Gly Tyr Lys Leu
405 410 415

Phe Gly Ser Thr Ser Ser Phe Cys Leu Ile Ser Gly Ser Ser Val Gln
420 425 430

Trp Ser Asp Pro Leu Pro Glu Cys Arg Glu Ile Tyr Cys Pro Ala Pro
435 440 445

-continued

Pro Gln Ile Asp Asn Gly Ile Ile Gln Gly Glu Arg Asp His Tyr Gly
450 455 460

Tyr Arg Gln Ser Val Thr Tyr Ala Cys Asn Lys Gly Phe Thr Met Ile
465 470 475 480

Gly Glu His Ser Ile Tyr Cys Thr Val Asn Asn Asp Glu Gly Glu Trp
485 490 495

Ser Gly Pro Pro Pro Glu Cys Arg Gly Lys Ser Leu Thr Ser Lys Val
500 505 510

Pro Pro Thr Val Gln Lys Pro Thr Thr Val Asn Val Pro Thr Thr Glu
515 520 525

Val Ser Pro Thr Ser Gln Lys Thr Thr Thr Lys Thr Thr Thr Pro Asn
530 535 540

Ala Gln Ala Thr Arg Ser Thr Pro Val Ser Arg Thr Thr Lys His Phe
545 550 555 560

His Glu Thr Thr Pro Asn Lys Gly Ser Gly Thr Thr Ser Gly Thr Thr
565 570 575

Arg ( 2 ) INFORMATION FOR SEQ ID NO:4:

( i ) SEQUENCE CHARACTERISTICS:
( A ) LENGTH: 13 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:4:

Ala Lys Arg Gly Leu Arg Arg Arg Leu Gly Arg Lys Ala
1 5 10

( 2 ) INFORMATION FOR SEQ ID NO:5:

( i ) SEQUENCE CHARACTERISTICS:
( A ) LENGTH: 6 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:5:

Ala Arg Arg Gly Lys Leu
1 5

( 2 ) INFORMATION FOR SEQ ID NO:6:

( i ) SEQUENCE CHARACTERISTICS:
( A ) LENGTH: 8 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:6:

Trp Gln Pro Pro Arg Ala Arg Ile
1 5

( 2 ) INFORMATION FOR SEQ ID NO:7:

( i ) SEQUENCE CHARACTERISTICS:
( A ) LENGTH: 6 amino acids
( B ) TYPE: amino acid ( C ) STRANDEDNESS: single
( D ) TOPOLOGY: linear ( i i ) MOLECULE TYPE: protein ( x i ) SEQUENCE DESCRIPTION: SEQ ID NO:7:

Leu Ile Gly Arg Lys Lys
1 5

( 2 ) INFORMATION FOR SEQ ID NO:8:

( i ) SEQUENCE CHARACTERISTICS:
( A ) LENGTH: 17 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:8:

Ala Lys Leu Asn Cys Arg Leu Tyr Arg Lys Ala Asn Lys Ser Ser Lys
1 5 10 15

Leu ( 2 ) INFORMATION FOR SEQ ID NO:9:

( i ) SEQUENCE CHARACTERISTICS:
( A ) LENGTH: 15 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:9:

Thr Ser Asp Gln Ile His Phe Phe Phe Ala Lys Leu Asn Cys Arg
1 5 10 15

( 2 ) INFORMATION FOR SEQ ID NO:10:

( i ) SEQUENCE CHARACTERISTICS:
( A ) LENGTH: 20 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:10:

Ser Glu Lys Thr Leu Arg Lys Trp Leu Lys Met Phe Lys Lys Arg Glu
1 5 10 15

Leu Glu Glu Tyr
20

( 2 ) INFORMATION FOR SEQ ID NO:11:

( i ) SEQUENCE CHARACTERISTICS:
( A ) LENGTH: 15 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:11:

His Arg His His Pro Arg Glu Met Lys Lys Arg Val Glu Asp Leu
1 5 10 15

-continued ( 2 ) INFORMATION FOR SEQ ID NO:12:

( i ) SEQUENCE CHARACTERISTICS:
( A ) LENGTH: 18 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:12:

Phe Arg Lys Leu Thr His Arg Leu Phe Arg Arg Asn Phe Gly Tyr Thr
1 5 10 15

Leu Arg ( 2 ) INFORMATION FOR SEQ ID NO:13:

( i ) SEQUENCE CHARACTERISTICS:
( A ) LENGTH: 12 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:13:

Leu Tyr Lys Lys Ile Leu Lys Lys Leu Leu Glu Ala
1 5 10

( 2 ) INFORMATION FOR SEQ ID NO:14:

( i ) SEQUENCE CHARACTERISTICS:
( A ) LENGTH: 26 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:14:

Asn Gly Leu Lys Arg Asp Lys Leu Gly Cys Glu Tyr Cys Glu Cys Arg
1 5 10 15

Pro Lys Arg Lys Leu Ile Pro Arg Leu Ser
20 25

( 2 ) INFORMATION FOR SEQ ID NO:15:

( i ) SEQUENCE CHARACTERISTICS:
( A ) LENGTH: 23 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:15:

Lys Thr Lys Arg Lys Arg Lys Lys Gln Arg Val Lys Ile Ala Tyr Glu
1 5 10 15

Glu Ile Phe Val Lys Asn Met
20

( 2 ) INFORMATION FOR SEQ ID NO:16:

( i ) SEQUENCE CHARACTERISTICS:
( A ) LENGTH: 23 amino acids
( B ) TYPE: amino acid
( C ) STRANDEDNESS: single
( D ) TOPOLOGY: linear -continued ( i i ) MOLECULE TYPE: protein ( x i ) SEQUENCE DESCRIPTION: SEQ ID NO:16:

```
Lys Lys Lys Lys Lys Met Pro Lys Leu Arg Phe Ala Ser Arg Ile Arg
1               5                   10                  15

Lys Ile Arg Lys Lys Gln Phe
            20
```

( 2 ) INFORMATION FOR SEQ ID NO:17:

( i ) SEQUENCE CHARACTERISTICS:
( A ) LENGTH: 1878 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:17:

```
CTGCTTTCCT CCGGAGAAAT AACAGCGTCT TCCGCGCCGC GCATGGAGCC TCCCGGCCGC    60
CGCGAGTGTC CCTTTCCTTC CTGGCGCTTT CCTGGGTTGC TTCTGGCGGC CATGGTGTTG   120
CTGCTGTACT CCTTCTCCGA TGCCTGTGAG GAGCCACCAA CATTTGAAGC TATGGAGCTC   180
ATTGGTAAAC CAAAACCCTA CTATGAGATT GGTGAACGAG TAGATTATAA GTGTAAAAAA   240
GGATACTTCT ATATACCTCC TCTTGCCACC CATACTATTT GTGATCGGAA TCATACATGG   300
CTACCTGTCT CAGATGACGC CTGTTATAGA GAAACATGTC CATATATACG GGATCCTTTA   360
AATGGCCAAG CAGTCCCTGC AAATGGGACT TACGAGTTTG GTTATCAGAT GCACTTTATT   420
TGTAATGAGG GTTATTACTT AATTGGTGAA GAAATTCTAT ATTGTGAACT TAAAGGATCA   480
GTAGCAATTT GGAGCGGTAA GCCCCCAATA TGTGAAAAGG TTTTGTGTAC ACCACCTCCA   540
AAAATAAAAA ATGGAAAACA CACCTTTAGT GAAGTAGAAG TATTTGAGTA TCTTGATGCA   600
GTAACTTATA GTTGTGATCC TGCACCTGGA CCAGATCCAT TTTCACTTAT TGGAGAGAGC   660
ACGATTTATT GTGGTGACAA TTCAGTGTGG AGTCGTGCTG CTCCAGAGTG TAAAGTGGTC   720
AAATGTCGAT TTCCAGTAGT CGAAAATGGA AAACAGATAT CAGGATTTGG AAAAAAATTT   780
TACTACAAAG CAACAGTTAT GTTTGAATGC GATAAGGGTT TTTACCTCGA TGGCAGCGAC   840
ACAATTGTCT GTGACAGTAA CAGTACTTGG GATCCCCCAG TTCCAAAGTG TCTTAAAGTG   900
TCGACTGACT GTGGCCTTCC CCCAGATGTA CCTAATGCCC AGCCAGCTTT GGAAGGCCGT   960
ACAAGTTTTC CCGAGGATAC TGTAATAACG TACAAATGTG AAGAAAGCTT TGTGAAAATT  1020
CCTGGCGAGA AGGACTCAGT GATCTGCCTT AAGGGCAGTC AATGGTCAGA TATTGAAGAG  1080
TTCTGCAATC GTAGCTGCGA GGTGCCAACA AGGCTAAATT CTGCATCCCT CAAACAGCCT  1140
TATATCACTC AGAATTATTT TCCAGTCGGT ACTGTTGTGG AATATGAGTG CCGTCCAGGT  1200
TACAGAAGAG AACCTTCTCT ATCACCAAAA CTAACTTGCC TTCAGAATTT AAAATGGTCC  1260
ACAGCAGTCG AATTTTGTAA AAAGAAATCA TGCCCTAATC CGGGAGAAAT ACGAAATGGT  1320
CAGATTGATG TACCAGGTGG CATATTATTT GGTGCAACCA TCTCCTTCTC ATGTAACACA  1380
GGGTACAAAT TATTTGGCTC GACTTCTAGT TTTTGTCTTA TTTCAGGCAG CTCTGTCCAG  1440
TGGAGTGACC CGTTGCCAGA GTGCAGAGAA ATTTATTGTC CAGCACCACC ACAAATTGAC  1500
AATGGAATAA TTCAAGGGGA ACGTGACCAT TATGGATATA GACAGTCTGT AACGTATGCA  1560
TGTAATAAAG GATTCACCAT GATTGGAGAG CACTCTATTT ATTGTACTGT GAATAATGAT  1620
GAAGGAGAGT GGAGTGGCCC ACCACCTGAA TGCAGAGGAA AATCTCTAAC TTCCAAGGTC  1680
CCACCAACAG TTCAGAAACC TACCACAGTA AATGTTCCAA CTACAGAAGT CTCACCAACT  1740
```

TCTCAGAAAA CCACCACAAA AACCACCACA CCAAATGCTC AAGCAACACG GAGTACACCT 1800

GTTTCCAGGA CAACCAAGCA TTTTCATGAA ACAACCCCAA ATAAAGGAAG TGGAACCACT 1860

TCAGGTACTA CCCGTTGA 1878

( 2 ) INFORMATION FOR SEQ ID NO:18:

( i ) SEQUENCE CHARACTERISTICS:
( A ) LENGTH: 73 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:18:

CAGAGAATTC TCAAGCTTTT CTACCTAGTC TTCTTCTTAG ACCTCTTTTA GCTCGGGTAG 60

TACCTGAAGT GGT 73

( 2 ) INFORMATION FOR SEQ ID NO:19:

( i ) SEQUENCE CHARACTERISTICS:
( A ) LENGTH: 31 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:19:

CAGAGGTACC ATGGAGCCTC CCGGCCGCCG C 31

( 2 ) INFORMATION FOR SEQ ID NO:20:

( i ) SEQUENCE CHARACTERISTICS:
( A ) LENGTH: 52 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:20:

CAGAGAATTC TCATAGTTTA CCTCTTCTAG CTCGGGTAGT ACCTGAAGTG GT 52

( 2 ) INFORMATION FOR SEQ ID NO:21:

( i ) SEQUENCE CHARACTERISTICS:
( A ) LENGTH: 103 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:21:

CAGAGAATTC TCACATATTT TTAACAAAAA TTTCTTCATA TGCTATTTTC ACTCTCTGCT 60

TCTTTCTTTT TCTTTTGGTT TTTCGGGTAG TACCTGAAGT GGT 103

( 2 ) INFORMATION FOR SEQ ID NO:22:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear -continued ( i i ) MOLECULE TYPE: DNA (genomic)

( x i ) SEQUENCE DESCRIPTION: SEQ ID NO:22:

ACTTCAGGTA CTACCCGTAA AACCAAAAGA 30

( 2 ) INFORMATION FOR SEQ ID NO:23:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:23:

TGAAGTCCAT GATGGGCATT TTGGTTTTCT TTTTCT 36

( 2 ) INFORMATION FOR SEQ ID NO:24:

( i ) SEQUENCE CHARACTERISTICS:
( A ) LENGTH: 34 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:24:

CAGAGAATTC TCACATATTT TTAACAAAAA TTTC 34

( 2 ) INFORMATION FOR SEQ ID NO:25:

( i ) SEQUENCE CHARACTERISTICS:
( A ) LENGTH: 58 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:25:

CAGAGAATTC TCATATTCTA GCTCTAGGAG GCTGCCATCG GGTAGTACCT GAAGTGGT 58

( 2 ) INFORMATION FOR SEQ ID NO:26:

( i ) SEQUENCE CHARACTERISTICS:
( A ) LENGTH: 55 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:26:

CAGAGAATTC TCAGGTTTTT TTTCTACCTA TTAGTCGGGT AGTACCTGAA GTGGT 55